United States Patent [19]

Cameron

[11] Patent Number: 5,203,347

[45] Date of Patent: Apr. 20, 1993

[54] UNI-CABLE DEFIBRILLATOR PADDLES

[75] Inventor: David B. Cameron, McMinnville, Oreg.

[73] Assignee: Hewlett-Packard Company, Palo Alto, Calif.

[21] Appl. No.: 626,651

[22] Filed: Dec. 12, 1990

[51] Int. Cl.⁵ ............................................. A61N 1/04
[52] U.S. Cl. .............................. 128/783; 128/419 D
[58] Field of Search ............... 128/419 D, 783, 798, 128/803

[56] References Cited

U.S. PATENT DOCUMENTS

| | | | |
|---|---|---|---|
| 3,196,877 | 7/1965 | Corbin | 128/419 D |
| 4,023,573 | 5/1977 | Pantridge et al. | 128/419 D |
| 4,097,113 | 6/1978 | McKeivy | 128/419 D |
| 4,848,345 | 7/1989 | Zenkich | 128/419 D |

Primary Examiner—William E. Kamm

[57] ABSTRACT

A uni-cable paddle system comprising two paddles with contact surfaces, and a main cable connected at one of its ends to one of the paddles, e.g., the sternum paddle. An inter-paddle cable connects the sternum and apex paddles. The main cable has two high-voltage (HV) wires. One of the HV wires is connected to the contact surface of the sternum paddle; the other HV wire is connected to the apex paddle's contact surface via a HV wire in the inter-paddle cable. Control switches and display indicators may be located on the paddles; the wires for these additional functions may be integrated into the main and inter-paddle cables.

6 Claims, 4 Drawing Sheets

UNI-CABLE DEFIBRILLATOR PADDLES

BACKGROUND OF THE INVENTION

1. Field of the Invention

The present invention relates to the field of medical defibrillators, and specifically to their paddles and cables.

2. Description of Related Art

A defibrillator reduced to its basic elements is a battery, a capacitor and two paddles connected to the capacitor. Ideally, the paddles would have unrestricted movement, the cables would not tangle, and both the paddles and cables would detach easily from the defibrillator for storage.

In a typical embodiment, each paddle is connected to a respective coiled cable having its other end attached to a single connector. Unfortunately, these two coiled cables can become tangled together during use, with potentially life-threatening results. Furthermore, due to the total length of cable required, storage of the paddles and cables can be difficult.

SUMMARY OF THE INVENTION

The present invention provides for a uni-cable paddle system for use with a defibrillator. The system comprises two paddles with contact surfaces and a main cable connected at one of its ends to one of the paddles, say the sternum paddle; its other end having a connector for attachment to the defibrillator. An inter-paddle cable extends between the sternum and apex paddles.

The main cable includes two high-voltage (HV) wires. One of these HV wires is connected to the contact surface of the sternum paddle, and the other HV wire is connected to the contact surface of the apex paddle via a HV wire in the inter-paddle cable.

In preferred embodiments, the main and inter-paddle cables are identical, having two HV wires arranged in a shielded, twisted pair to minimize external electromagnetic interference. The "unused" HV wire in the inter-paddle cable may be connected to the sternum contact surface (but left unconnected at its other end) to minimize common mode effects in the cable and to match capacitances between the apex and sternum paddles and ground.

In preferred embodiments, charge and discharge switches may be located on the paddles, as well as charge done and paddle contact indicators. The wires for these additional functions may be integrated into the main and inter-paddle cables. For the case where the main and inter-paddle cables are identical, any control wires needed between the defibrillator and the sternum paddle, but unnecessary between the apex and sternum paddles, can remain unconnected at both ends of the inter-paddle cable.

It is a principal object of the present invention to provide a defibrillator cable and paddle system which minimizes cable tangling during use and storage.

Another object of the present invention is to provide a defibrillator cable and paddle system which produces a minimum of electromagnetic interference.

The foregoing and other objects, features and advantages of the invention will become more readily apparent from the following detailed description of a preferred embodiment which proceeds with reference to the drawings.

DETAILED DESCRIPTION OF THE PREFERRED EMBODIMENTS

Figure 1:
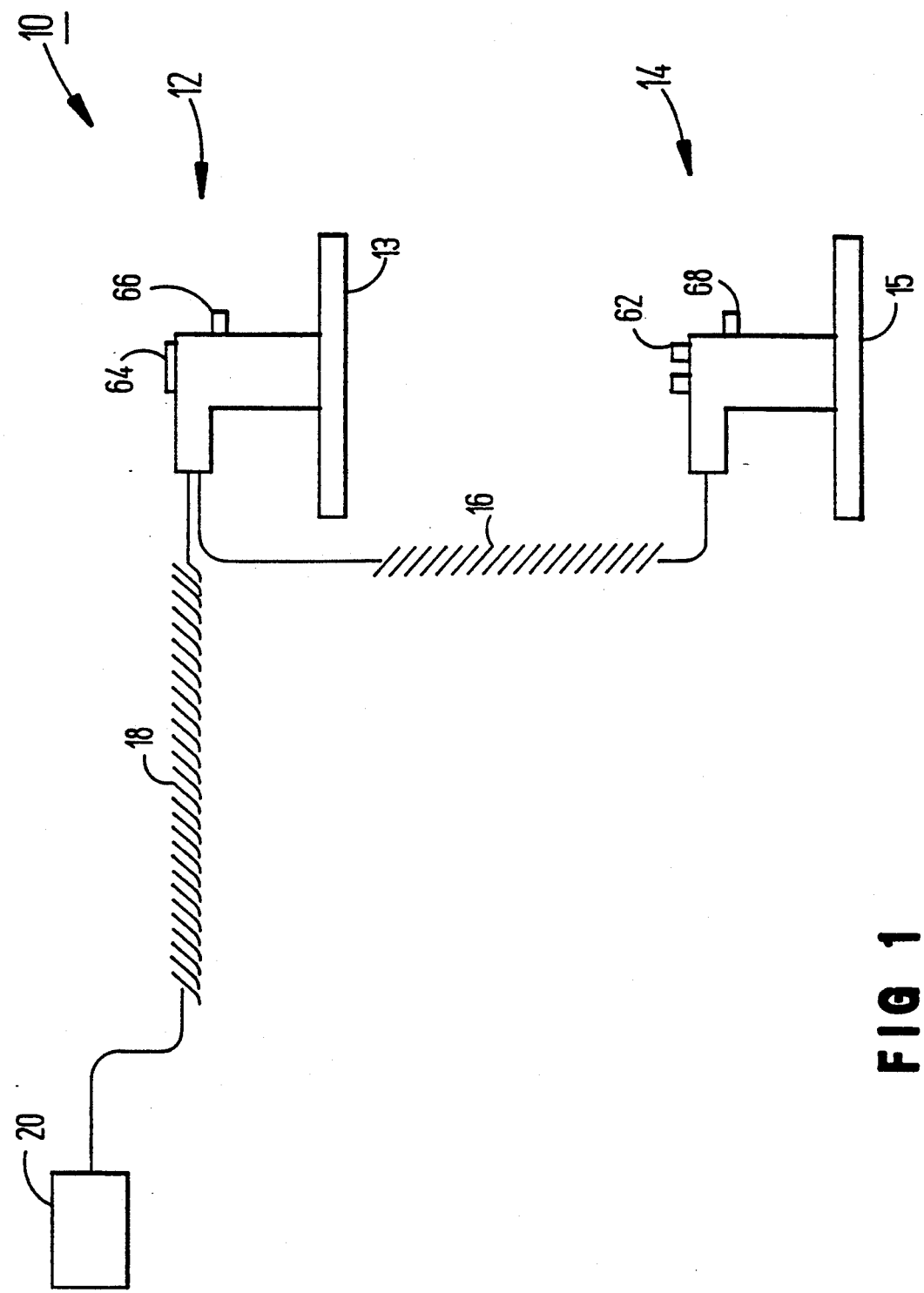
FIG. 1 is a simplified block diagram of a first embodiment of a uni-cable defibrillator paddle system according to the present invention.

Referring now to the drawings, FIG. 1 shows a first embodiment of a uni-cable defibrillator paddle system 10 according to the present invention. The system includes a sternum paddle 12 connected to an apex paddle 14 by an inter-paddle cable 16. A main cable 18 is connected to the sternum paddle and terminates in a connector 20 for connection with a defibrillator (not shown). The cables 16, 18 preferably are coiled to take up any slack during use and thereby minimize any tangling. The sternum and apex paddles have respective contact surfaces 13, 15 for establishing an electrical circuit with a patient.

Preferably, the apex paddle 12 has a charge switch 60 mounted thereon to prepare the defibrillator for discharge. When the capacitor is charged, the defibrillator activates a charge done indicator 62 on the apex paddle. A paddle contact indicator 64 on the sternum paddle 12 shows the quality of paddle contact before discharge. Two discharge switches 66, 68 mounted on the paddles enable the defibrillator to be discharged. The switches preferably are wired in series, requiring both to be depressed before discharge occurs.

Figure 2:
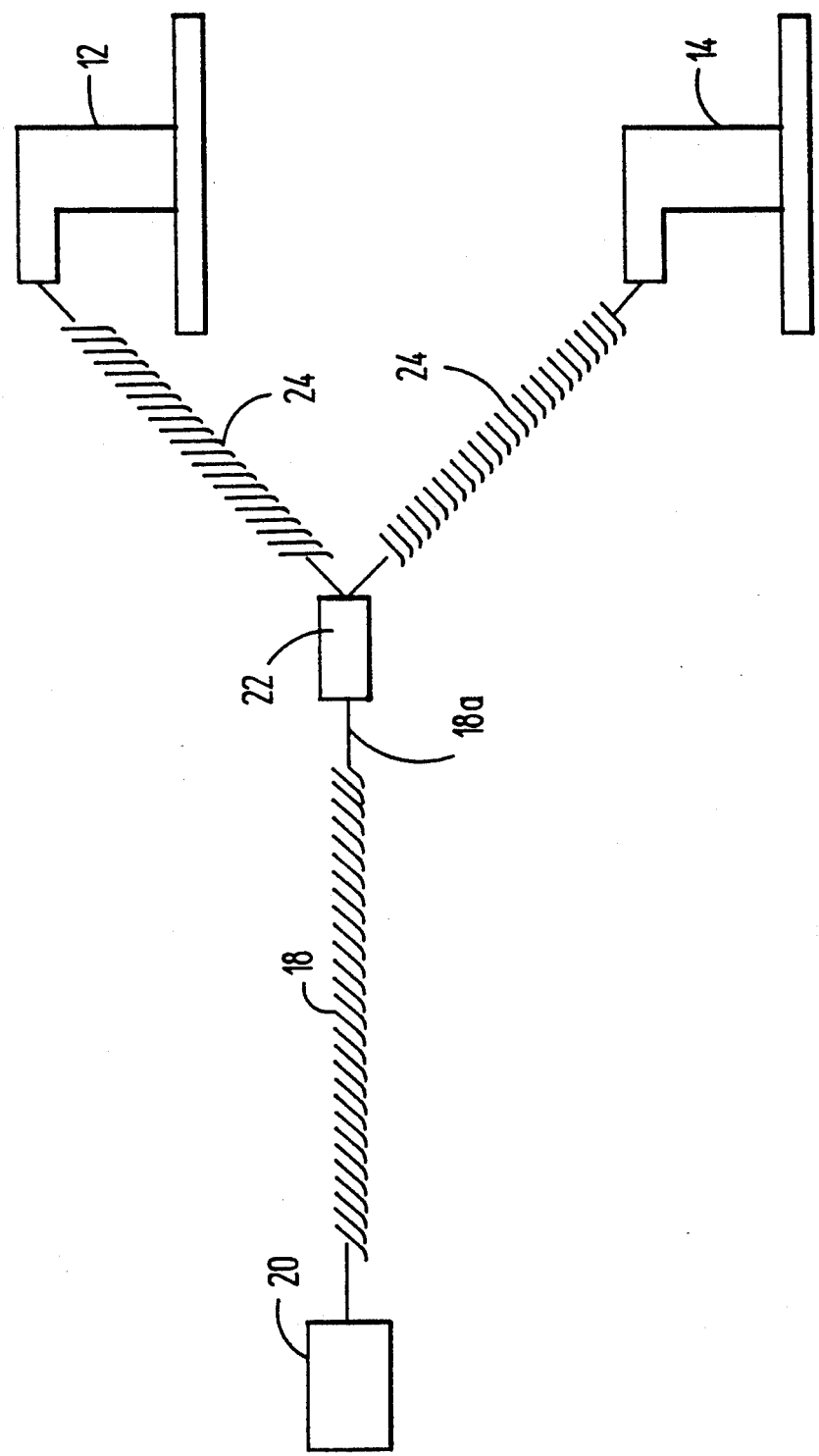
FIG. 2 is a simplified block diagram of a second embodiment of a uni-cable defibrillator paddle system according to the present invention.

An alternative embodiment, shown in FIG. 2 includes a main cable 18 terminating in a connector 20 for connection with a defibrillator. The main cable's other end 18a terminates at a junction box 22. Secondary cables 24 connect the sternum paddle 12 and the apex paddle 14 to the junction box 22. The paddles preferably would have the same switches and indicators discussed above for FIG. 1.

Figure 3:
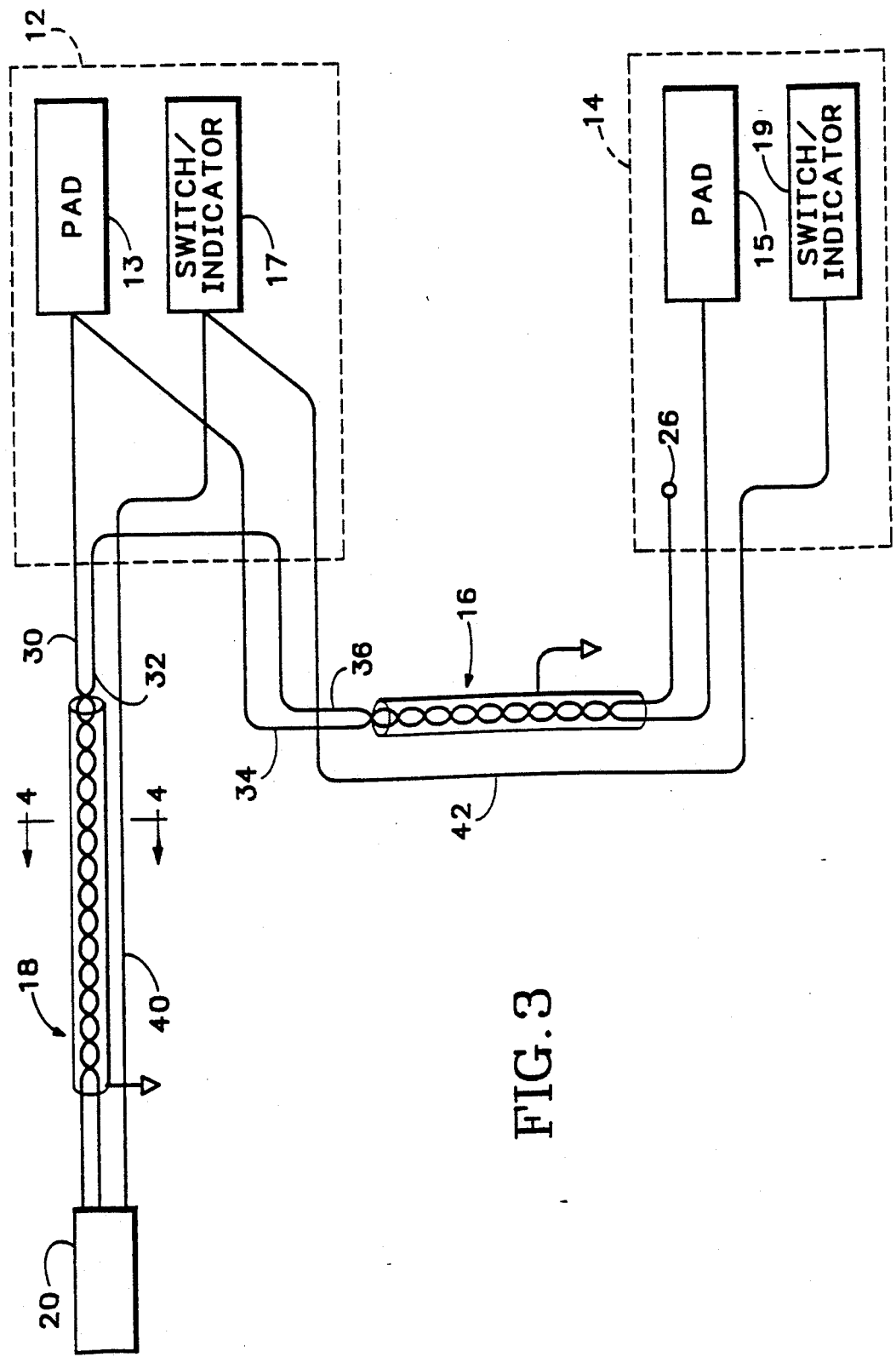
FIG. 3 is a electrical block diagram of the system of FIG. 1.

Referring to FIG. 3, the electrical connections for the uni-cable paddle system of FIG. 1 are shown. The sternum and apex paddles 12 and 14 are shown interconnected by the inter-paddle cable 16. The sternum paddle is also connected to the connector 20 with the main cable 18. Both the main and inter-paddle cables include two high-voltage (HV) wires arranged as a shielded, twisted pair. One of the HV wires 30 contained in the main cable is attached to the sternum paddle's contact surface 13. The main cable's other HV wire 32 passes through the sternum paddle and is connected to the apex paddle's contact surface 15 via a HV wire 36 contained in the inter-paddle cable. The "unused" HV wire 34 is connected to the sternum paddle's contact surface and left open-circuited 26 in the apex paddle. This minimizes common mode effects in the cable and better matches capacitances between the apex and sternum paddles and ground.

The main and inter-paddle cables 16, 18 also may include control wires 40, 42. These wires may be connected to switches and indicators 17, 19 located on the paddles.

The uni-cable paddle system includes a first switch 17 on said sternum paddle 12 and a second switch 19 on the apex paddle 14. The main cable 18 includes a second wire 30 connected to the first switch 17. The inter-paddle cable 16 includes a second control wire 42 which is connected to the first switch 17 and the second switch 19.

Figure 4:
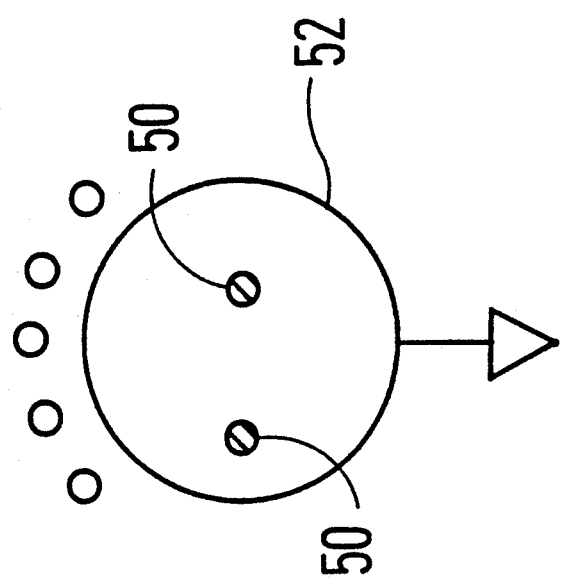
FIG. 4 is a cross-sectional diagram of a cable along line 4—4 of FIG. 3.

Referring now to FIG. 4, the main and inter-paddle cables preferably comprise two HV wires 50 enclosed in a grounded shield 52. Surrounding this shield are any control wires 54 necessary for proper operation of control switches and indicators on the paddles.

Throughout this disclosure, the uni-cable system has been described having the main cable connected to the sternum paddle. It will be understood that, alternatively, the main cable can be connected to the apex paddle. These and other variations and modifications on the described embodiments can be made on the present invention, the scope of which is limited only by the following claims.

I claim:

1. A uni-cable paddle system for a defibrillator, comprising:
   (a) first and second paddle means, each having a contact surface, for establishing an electrical connection with a patient;
   (b) a main cable having a first and second high-voltage wires, said main cable having a first end for connection to the defibrillator and having a second end connected to said first paddle means, wherein said first high-voltage wire is connected to said contact surface of said first paddle means;
   (c) an inter-paddle cable having a third high-voltage wire, said third high-voltage wire having a first end connected to said second high voltage wire of said main cable and having a second end connected to said contact surface of said second paddle means.

2. The uni-cable paddle system of claim 1, further comprising a switch on said first paddle means, and wherein said main cable further includes a control wire connected to said switch.

3. The uni-cable paddle system of claim 1, further comprising a switch on said second paddle means, and wherein said main cable further includes a first control wire, said inter-paddle cable further includes a second control wire, said second control wire connected to said first control wire and to said switch.

4. The uni-cable paddle system of claim 1, wherein said first and second high-voltage wires form a twisted pair.

5. The uni-cable paddle system of claim 1, wherein said main and inter-paddle cables are helical coiled.

6. The uni-cable paddle system of claim 1, wherein said interpaddle cable further includes a fourth high-voltage wire having a first end and a second end, said first end of said high-voltage wire connected to said contact surface of said first paddle means and said second end open-circuited.

* * * * *